United States Patent [19]

Myers

[11] 4,228,676
[45] Oct. 21, 1980

[54] ASH SAMPLING PROBE
[75] Inventor: John G. Myers, Pittsburgh, Pa.
[73] Assignee: Calgon Corporation, Pittsburgh, Pa.
[21] Appl. No.: 41,840
[22] Filed: May 23, 1979
[51] Int. Cl.³ .......................... G01N 1/04; G01N 1/22
[52] U.S. Cl. ...................................................... 73/28
[58] Field of Search .................. 73/421.5 R, 421.5 A, 73/28

[56] References Cited
U.S. PATENT DOCUMENTS

| | | | |
|---|---|---|---|
| 1,890,592 | 12/1932 | Stein et al. | 73/421.5 A |
| 3,885,437 | 5/1975 | Reagan | 73/421.5 A |
| 4,015,479 | 4/1977 | Apple | 73/422 R |

FOREIGN PATENT DOCUMENTS 1499984 9/1967 France ................................ 73/421.5 R

OTHER PUBLICATIONS

Fuel Oil Treatment, Oil Ash Sampling and pH Testing, Calgon Corporation, Technical Information Report No. Fc-107, Jan. 1975.

Primary Examiner—S. Clement Swisher
Attorney, Agent, or Firm—Mario A. Monaco; Martin L. Katz; Raymond M. Speer

[57] ABSTRACT

Improved probe for collecting oil ash samples having a porous, closed end tube.

10 Claims, 2 Drawing Figures

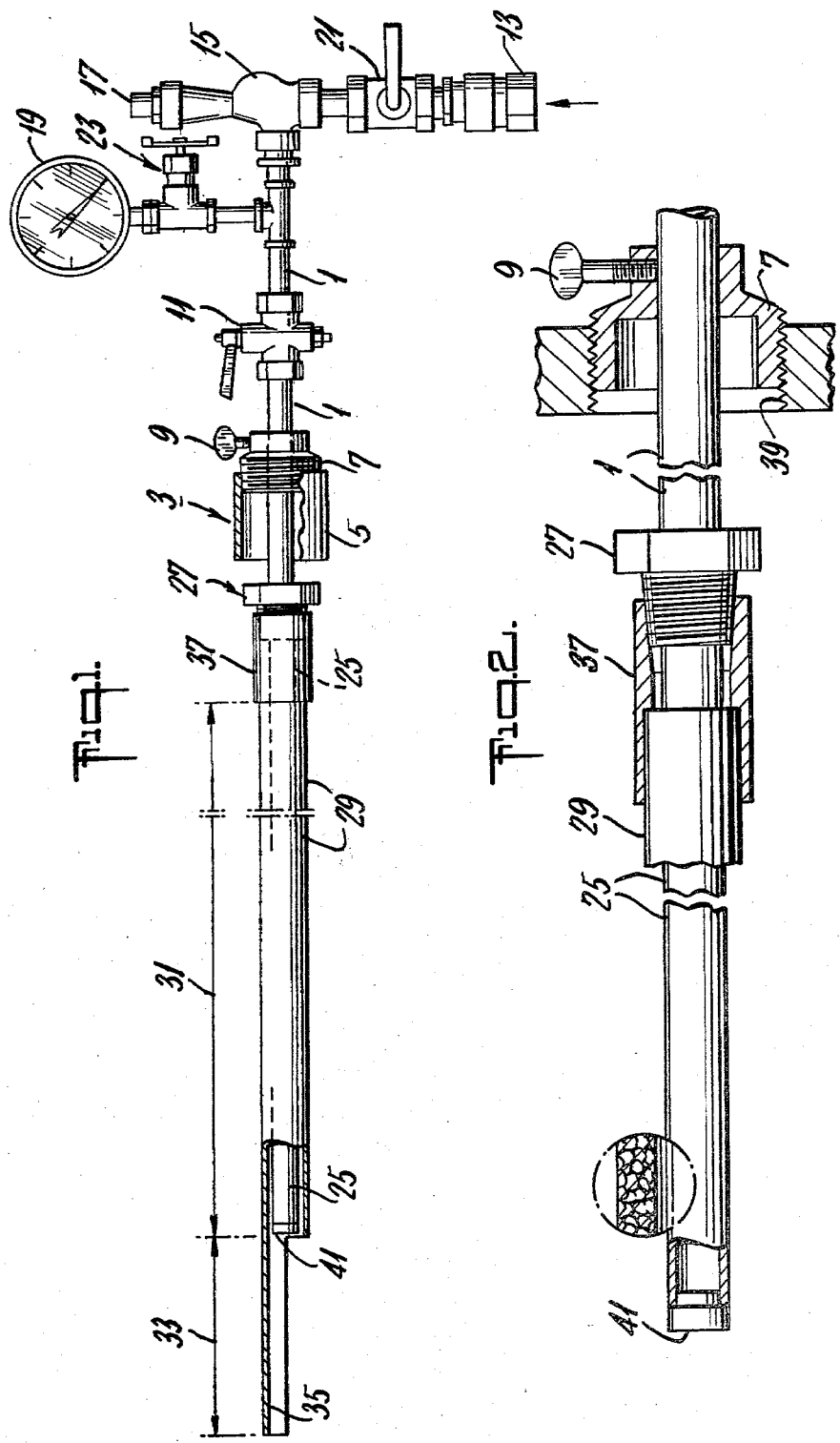

ASH SAMPLING PROBE

BACKGROUND OF THE INVENTION

1. Field of the Invention

The present invention is concerned with a probe for collecting ash samples, especially oil ash samples from gases located in a wall confined region, such as stack emission gases. The probe utilizes a tube which, when inserted into the stream of gas to be sampled, withdraws a portion of said stream by reason of reduced pressure applied to said tube. Ash carried by the stream of gas is collected by means of a porous, closed end tube attached to the end of the tube for withdrawing the portion of the emission gas stream.

2. Brief Description of the Prior Art

Heretofore, ash sampling probes of the type for which the probe of the present invention constitutes an improvement, employed screen filters within an open end tube to collect the ash samples. See, for example, Calgon Corporation's Technical Information Report No. FC-107 (January 1975). However, such an arrangement has resulted in several serious disadvantages. Such screen filters often become plugged, thus preventing an even rate of deposit of the ash on the filter. Smaller particles of ash and other materials often pass through the screen filters, resulting in clogging which interferes with proper functioning of the pressure gauge and other parts of the probe apparatus. And, a number of hours are required to collect an adequate ash sample for testing. The ash sampling probe of the present invention overcomes these serious disadvantages by replacing the screen filters within an open end tube with a porous, closed end tube.

Reagan U.S. Pat. No. 3,885,437 describes a device for sampling exhaust stack effluent in which a vacuum operated probe captures a portion of an effluent to be sampled and conveys it to a container having filters for removing the particulate matter from the captured effluent. However, this device does not teach or suggest the improved probe of the present invention.

Apple U.S. Pat. No. 4,015,479 describes a remote sampling probe for withdrawing fluid from a pipe through a filter capped sample tube extending into the pipe. However, this device does not teach or suggest the improved probe of the present invention.

SUMMARY OF THE INVENTION

In accordance with the present invention there is provided an improved ash sampling probe comprising:

(a) a gas stream withdrawing tube having a first end through which the gas stream bearing ash to be sampled is withdrawn;

(b) a port engaging coupling adjustably mounted around the gas stream withdrawing tube whereby the latter may be moved into a wall confined region containing the ash bearing gas stream through a port in said wall, while maintaining a gas-tight association between said withdrawing tube and other parts of the probe and the wall confined region;

(c) means for applying reduced pressure to a second end of the gas stream withdrawing tube, whereby the ash bearing gas stream is caused to move through said tube, and associated with said means, valving means connecting said means for applying reduced pressure to said second end of said withdrawing tube;

wherein the improvement comprises;

(d) attached to said first end of said gas stream withdrawing tube, a porous closed end tube which permits the ash bearing gas stream to pass therethrough and into said withdrawing tube, while retaining on the outer surface thereof, the ash contained in said ash bearing gas stream; and (e) associated with the porous closed end tube, a collecting baffle which directs particles of ash contained in the ash bearing gas stream toward the porous closed end tube.

In accordance with the present invention there is also provided an improved method of sampling ash contained in an ash bearing gas stream located in a wall confined region, comprising the steps of (a) providing a gas stream withdrawing tube having a first end through which the gas stream bearing ash to be sampled is withdrawn;

(b) providing a port engaging coupling adjustably mounted around the gas stream withdrawing tube and moving the latter into a wall confined region containing the ash bearing gas stream through a port in said wall, while maintaining a gas-tight association between said withdrawing tube and other parts of the probe and the wall confined region;

(c) applying reduced pressure to a second end of the gas stream withdrawing tube, whereby the ash bearing gas stream is caused to move through said tube, wherein the improvement comprises:

(d) providing a porous closed end tube attached to said first end of said stream withdrawing tube, whereby the ash bearing gas stream passes through said porous closed end tube while the latter retains on the outer surface thereof the ash contained in said ash bearing gas stream; and (e) providing a collecting baffle associated with the porous closed end tube, whereby particles of ash contained in the ash bearing gas stream are directed toward the porous closed end tube.

BRIEF DESCRIPTION OF THE DRAWINGS

The ash sampling probe of the present invention is illustrated in the following figures in which:

FIG. 1 is a partially exposed side view of the ash sampling probe of the present invention; and FIG. 2 is an enlarged, partially exposed side view of the collecting baffle and porous closed end tube assembly.

DESCRIPTION OF THE PREFERRED EMBODIMENT

Although the ash sampling probe of the present invention may be employed in a number of different situations, to collect ash samples from a gas stream, the preferred use of the ash sampling probe of the present invention is to collect oil ash samples from industrial flue gases. For such uses, the preferred embodiment of the ash sampling probe of the present invention is illustrated in FIG. 1. The gas stream withdrawing tube 1 has mounted around it the port engaging coupling 3. The purpose of this coupling is to provide a gas-tight association between the withdrawing tube 1 and the port (not shown) of a wall (not shown) which confines the ash bearing gas stream from which the ash sample will be taken, for example, an industrial flue pipe. The port engaging coupling 3 consists of a sleeve portion 5 threadingly engaged to a cored square head plug 7 through which withdrawing tube 1 passes. The cored square head plug 7 is drilled and tapped so as to receive wing plug 9, which may be rotated so as to engage withdrawing tube 1 and thereby firmly engage the port engaging coupling 3 to the withdrawing tube 1. In fact, since the port engaging coupling 3 is already firmly attached to the port of an industrial flue pipe, rotation of the wing plug 9 to a disengaged position permits movement of the withdrawing tube 1 and associated apparatus of the entire probe in and out of the flue pipe until the desired position is obtained, when the withdrawing tube 1 is fixed in position by rotation of wing plug 9 to an engaging position with withdrawing tube 1. Use of the wing plug 9 also permits rotation of the withdrawing tube 1 so that it can be properly positioned with respect to the collecting baffle 29, described below.

Once the withdrawing tube 1 and the other associated apparatus of the probe have been fixed in position by means of the wing plug 9 in the port engaging coupling 3, the valve 11 is closed, segregating withdrawing tube 1 from the remaining portions of the probe. A source of pressurized air is then attached to the probe by means of coupling 13. The pressurized air travels through ejector 15 which contains a venturi valve (not shown) by means of which a reduced pressure zone or vacuum is created in withdrawing tube 1. Once this is accomplished, the air then escapes through outlet 17. The extent of reduced pressure created is measured by means of the standard vacuum guage 19, graduated in inches of water or mercury. Once the desired level of reduced pressure is obtained, by adjusting valve 21, the valve 23 may be closed and the valve 11 opened. The reduced pressure will cause an ash bearing gas stream to enter the withdrawing tube 1 by passing through the porous closed end tube 25. The ash contained in the gas stream will adhere to the outside of the porous closed end tube 25.

The porous closed end tube 25, preferably made of sintered stainless steel, is welded to the inside of the cored reducing bushing 27. Associated with the porous closed end tube 25 is a collecting baffle 29. This baffle has a closed portion 31 and an open portion 33. The open portion 33, shown as a half, or semicircular cutaway tube, is oriented so that the inside 35 of the open portion 33 faces against the movement of the ash bearing gas stream. In this way, particles in the gas stream will impinge upon the inside 35 of the collecting baffle 29 and be directed toward, or available to, the porous closed end tube 25. The porous closed end tube 25 is contained wholly inside the closed portion 31 of the collecting baffle 29. The collecting baffle 29 is attached to the reducing bushing 27 by means of sleeve 37 which is threadingly engaged to both the baffle 29 and the bushing 27.

FIG. 2 is an enlarged view of the improved portion of the ash sampling probe of the present invention. The withdrawing tube 1 is held firmly in position in the cored square head plug 7 by the wing plug 9. The cored square head plug 7, in turn, is threadingly engaged to the port opening 39. Alternatively, where the port opening is not threaded to accommodate coupling in this manner, the sleeve portion 5 of the port engaging coupling 3 may additionally be employed.

The withdrawing tube 1 terminates at one end of the reducing bushing 27 to which it is welded. To the opposite end of the bushing 27 there is welded the porous closed end tube 25, which is made of sintered stainless steel. Welded to the end of porous closed end tube 25 is a solid end cap 41, also made of stainless steel. Surrounding the porous closed end tube 25 is the collecting baffle 29, which is attached to the bushing 27 by means of sleeve 37.

One of the improvement features of the ash sampling probe of the present invention is the porous closed end tube. In the preferred embodiment, the porous closed end tube is made of sintered stainless steel, for example that available from Mott Metallurgical Corp., Farmington, Conn., as Std. Model 1400. The end of the porous stainless steel tube must be closed with a solid end cap which, suitably, is welded in place by means of arc welding or silver solder techniques.

The porous closed end tube can also be fabricated from other suitable materials. For example, the tube could be made of a porous ceramic or glass frit. It is only required that the tube be sufficiently porous to permit the ash bearing gas stream to pass through it, while having pores small enough to be impervious to passage of the fine particles of ash in the gas stream, which then collect on the outside of the porous closed end tube. Preferably, of course, the material from which the porous closed end tube is fabricated will be corrosion and heat resistant.

One of the chief advantages of the improved ash sampling probe of the present invention lies in the ability of the porous closed end tube to rapidly and efficiently collect a representative ash sampling of sufficient size for testing. No problems are experienced with clogging of the porous closed end tube, as has been the case heretofore when filter devices were employed. An adequate ash sample may be collected in as little time as one hour or less. Also, the size of the porous closed end tube is easily varied. A sintered stainless steel tube, for example, may be obtained in lengths of thirty-six inches and then cut to any suitable length, such as six inches, which is preferred. The length may be varied to accommodate differing ash concentrations and velocities in the ash bearing gas streams, or the need for greater or smaller ash samples.

Another feature of the improved ash sampling probe of the present invention is the collecting baffle, which ensures that a representative sample of ash is collected for testing, and also contributes to a more rapid collection of the ash sample.

When the improved ash sampling probe of the present invention is utilized, it is first necessary to determine the exact length of the probe required for optimum ash sample collection. The length of the probe may be varied from two to six feet by means of two foot threaded sections and couplings. These are not shown in the drawings, but when employed would be installed between valve 11 and the reducing bushing 27 in FIG. 1 of the drawings.

The exact length of the probe may be determined by one of two techniques. The first method uses the probe to measure the pressure difference at several points across the area traversed by the sample port. The point of the greatest pressure drop indicates the maximum gas flow, and the ash sampling probe is inserted in such a way that the porous closed end tube will be at the area of maximum pressure differential. The second method is based on trial and error. Several ash samples are collected at various probe lengths and their weights are measured and recorded. The length of probe is selected which yields the largest quantity of ash sample in the shortest time.

Once a sample of ash is collected, it is removed for testing by first removing the collecting baffle and then tapping and/or brushing the ash from the surface of the porous closed end tube. The ash may be tested for pH or other characteristics which indicate those fuel additives that may be required for improved combustion and control of corrosion with regard to the ash bearing gas stream and the fuel from which it has been generated in the equipment concerned.

What is claimed is:

1. In a probe for sampling ash contained in an ash bearing gas stream located in a wall confined region, said probe comprising
   (a) a gas stream withdrawing tube having a first end through which the gas stream bearing ash to be sampled is withdrawn;
   (b) a port engaging coupling adjustably mounted around the gas stream withdrawing tube whereby the latter may be moved into a wall confined region containing the ash bearing gas stream through a port in said wall, while maintaining a gastight association between said withdrawing tube and the wall confined region;
   (c) means for applying reduced pressure to a second end of the gas stream withdrawing tube, whereby the ash bearing gas stream is caused to move through said tube, and associated with said means, valving means connecting said means for applying reduced pressure to said second end of said withdrawing tube;
the improvement wherein said probe further comprises:
   (d) attached to said first end of said gas stream withdrawing tube, a porous closed end tube which permits the ash bearing gas stream to pass therethrough and into said withdrawing tube, while retaining on the outer surface thereof, ash contained in said ash bearing gas stream; and
   (e) associated with the porous closed end tube, a collecting baffle which directs particles of ash contained in the ash bearing gas stream toward the porous closed end tube.

2. The probe of claim 1 wherein the porous closed end tube is made of sintered stainless steel.

3. The probe of claim 1 wherein the collecting baffle comprises a tube having a closed portion in which the porous closed end tube is wholly contained, and an open portion which is a semicircular cutaway of the tube comprising said collecting baffle.

4. The probe of claim 1 wherein the wall confined region is an industrial flue pipe and the ash bearing gas stream is an industrial flue gas.

5. The probe of claim 1 wherein the ash contained in the ash bearing gas is oil ash.

6. In a method of sampling ash contained in an ash bearing gas stream located in a wall confined region, comprising the steps of
   (a) providing a gas stream withdrawing tube having a first end through which the gas stream bearing ash to be sampled is withdrawn;
   (b) providing a port engaging coupling adjustably mounted around the gas stream withdrawing tube and moving the latter into a wall confined region containing the ash bearing gas stream through a port in said wall, while maintaining a gas-tight association between said withdrawing tube and other parts of the probe and the wall confined region;
   (c) applying reduced pressure to a second end of the gas stream withdrawing tube, whereby the ash bearing gas stream is caused to move through said tube;
the improvement comprising the steps of:
   (d) providing a porous closed end tube attached to said first end of said gas stream withdrawing tube, whereby the ash bearing gas stream passes through said porous closed end tube while the latter retains on the outer surface thereof the ash contained in said ash bearing gas stream; and
   (e) providing a collecting baffle associated with the porous closed end tube, whereby particles of ash contained in the ash bearing gas stream are directed toward the porous closed end tube.

7. The method of claim 6 wherein the porous closed end tube is made of sintered stainless steel.

8. The method of claim 6 wherein the collecting baffle comprises a tube having a closed portion in which the porous closed end tube is wholly contained, and an open portion which is a semicircular cutaway of the tube comprising said collecting baffle.

9. The method of claim 6 wherein the wall confined region is an industrial flue pipe and the ash bearing gas stream is an industrial flue gas.

10. The method of claim 6 wherein the ash contained in the ash bearing gas is oil ash.

* * * * *